United States Patent

Bouhour et al.

[11] Patent Number: 5,931,856
[45] Date of Patent: Aug. 3, 1999

[54] ACTIVE IMPLANTABLE MEDICAL DEVICE HAVING DUAL CHAMBER CARDIAC STIMULATION AND A FALLBACK MODE

[75] Inventors: Anne Bouhour, Ville D'Auray; Marcel Limousin, Montrouge, both of France

[73] Assignee: ELA Medical S.A., Montrouge, France

[21] Appl. No.: 08/976,396

[22] Filed: Nov. 21, 1997

[30] Foreign Application Priority Data

Nov. 22, 1996 [FR] France .................................. 96 14270

[51] Int. Cl.⁶ ................................................. A61N 1/362
[52] U.S. Cl. ......................................................... 607/9
[58] Field of Search ........................................ 607/4, 9, 14

[56] References Cited

U.S. PATENT DOCUMENTS

| | | |
|---|---|---|
| 4,343,311 | 8/1982 | Markowitz . |
| 4,344,437 | 8/1982 | Markowitz . |
| 4,378,020 | 3/1983 | Nappholz et al. . |
| 4,412,541 | 11/1983 | Schaldach et al. . |
| 4,429,697 | 2/1984 | Nappholz et al. . |
| 4,432,362 | 2/1984 | Leckrone et al. . |
| 4,467,810 | 8/1984 | Vollman . |
| 4,515,161 | 5/1985 | Wittkampf et al. . |
| 4,554,920 | 11/1985 | Baker, Jr. et al. . |
| 4,554,921 | 11/1985 | Boute et al. . |
| 4,712,556 | 12/1987 | Baker et al. . |
| 4,714,079 | 12/1987 | Hedberg et al. . |
| 4,781,194 | 11/1988 | Elmqvist . |
| 4,788,980 | 12/1988 | Mann et al. . |
| 4,890,617 | 1/1990 | Markowitz et al. . |
| 4,932,406 | 6/1990 | Berkovits . |
| 4,944,298 | 7/1990 | Sholder . |
| 4,967,746 | 11/1990 | Vandegriff . |
| 5,226,415 | 7/1993 | Girodo et al. . |
| 5,312,451 | 5/1994 | Limousin et al. . |
| 5,374,280 | 12/1994 | Den Dulk . |
| 5,514,161 | 5/1996 | Limousin . |
| 5,540,726 | 7/1996 | Bonnet et al. . |
| 5,584,867 | 12/1996 | Limousin et al. . |
| 5,713,928 | 2/1998 | Bonnet et al. .............................. 607/9 |

FOREIGN PATENT DOCUMENTS

| | | |
|---|---|---|
| 318304 | 5/1989 | European Pat. Off. . |
| 488 840-A1 | 6/1992 | European Pat. Off. ....... A61N 1/368 |
| 661076-A1 | 12/1994 | European Pat. Off. ....... A61N 1/368 |
| 676216-A1 | 10/1995 | European Pat. Off. ....... A61N 1/368 |
| 676217-A1 | 10/1995 | European Pat. Off. ....... A61N 1/368 |
| 726082-A2 | 8/1996 | European Pat. Off. ....... A61N 1/368 |
| 755696-A2 | 1/1997 | European Pat. Off. ....... A61N 1/368 |
| WO 95/32758 | 12/1995 | WIPO .......................... A61N 1/368 |

*Primary Examiner*—William E. Kamm
*Assistant Examiner*—George R. Evanisko
*Attorney, Agent, or Firm*—Orrick, Herrington & Sutcliffe LLP

[57] ABSTRACT

An active implantable medical device, particularly of the cardiac pacemaker, defibrillator and/or cardiovertor type, having a function of dual chamber cardiac stimulation and a mode of fallback in which a mode of de-synchronisation of the ventricular stimulation occurs when the atrial rhythm exceeds an acceptable level, and a mode of progressive re-synchronisation occurs in the case of a return of the atrial rhythm to the acceptable level. The re-synchronisation is controlled in a conditional manner to be triggered and maintained only if (a) one detects no trouble of the atrial rhythm. In an alternate embodiment the re-synchronisation is triggered and maintained only if, in addition to condition (a): (b) one detects (20) the presence of an effective sinus rhythm. In another alternate embodiment, the re-synchronisation is triggered and maintained only if, in addition to conditions (a) and (b): (c) one determines that the duration between the end of the post-atrial atrial refractory period and the end of the atrial escape interval is at least equal to a predetermined duration during a number of successive cycles in the course of the re-synchronisation mode.

13 Claims, 1 Drawing Sheet

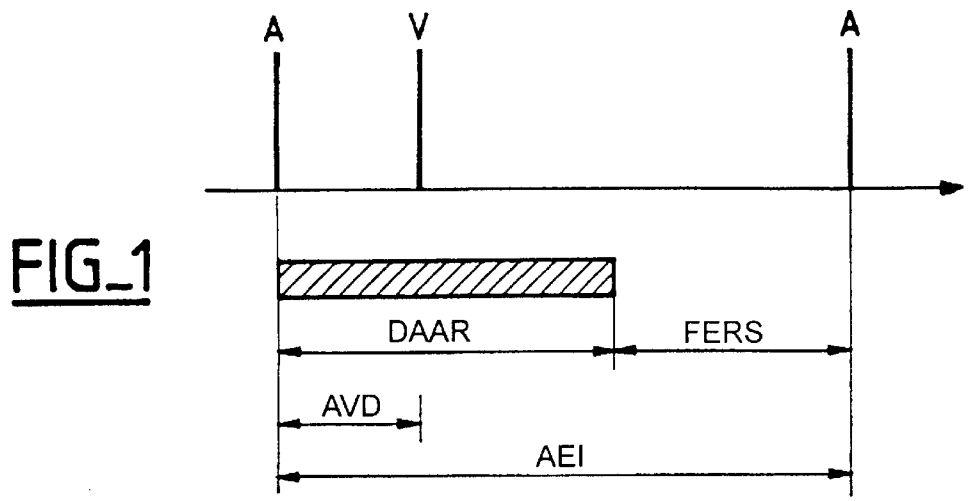
FIG_1
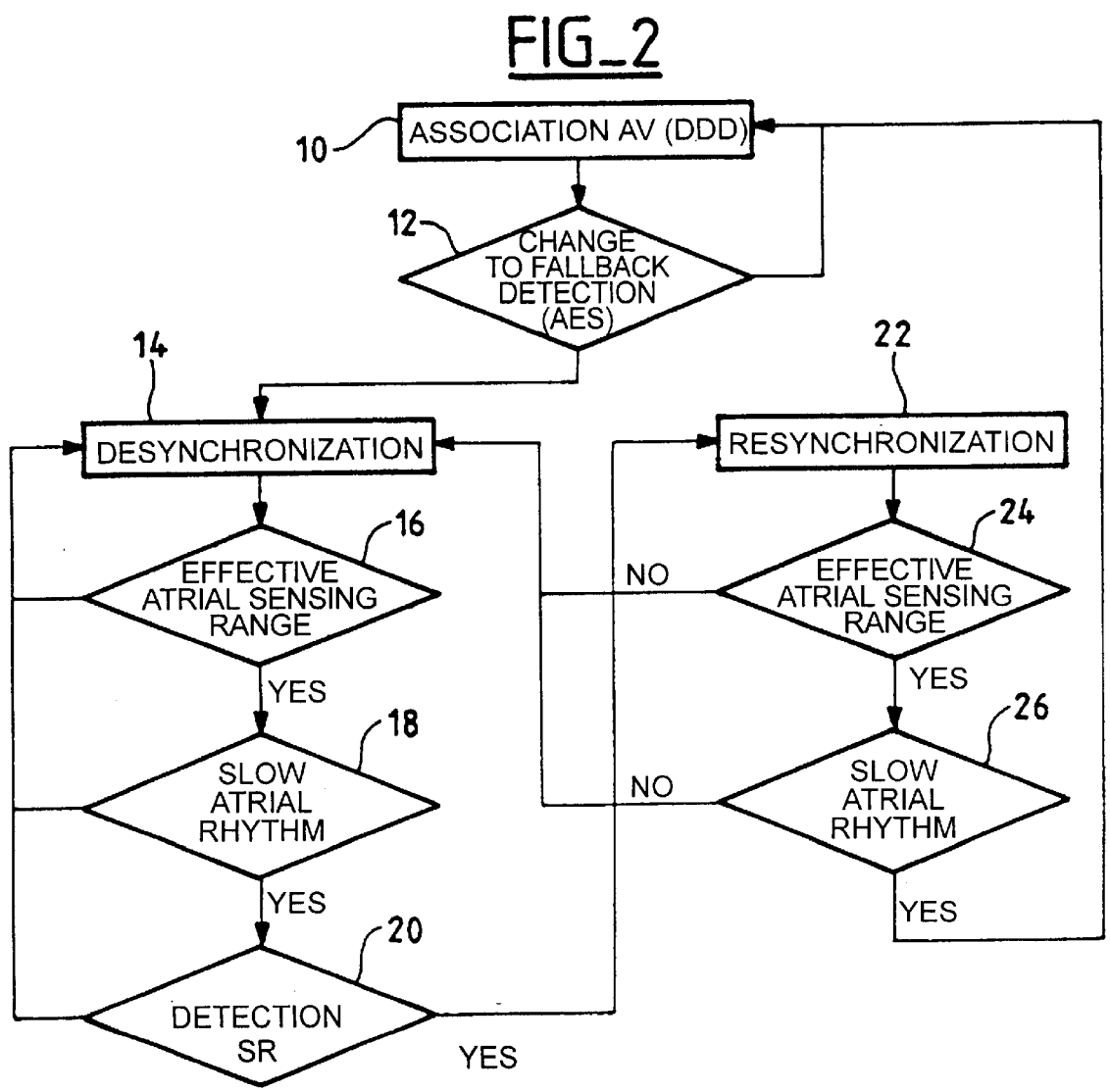
FIG_2

ACTIVE IMPLANTABLE MEDICAL DEVICE HAVING DUAL CHAMBER CARDIAC STIMULATION AND A FALLBACK MODE

FIELD OF THE INVENTION

The present invention concerns "active implantable medical devices" such as those defined by the Jun. 20, 1990 Directive 90/385/EEC of the European Community Council, more particularly to cardiac pacemakers, defibrillators and/or cardiovertors having a dual chamber cardiac stimulation function for the treatment of troubles of the atrial rhythm.

BACKGROUND OF THE INVENTION

The present invention is directed to a known cardiac pacing function, the so called "fallback" mode, and the resynchronisation of the cardiac ventricular stimulation to the atrial rhythm when the atrial rate returns to normal at the end of a phase of fallback.

The fallback mode and resynchronization have particularly been discussed in FR-A-2,544,989 as well as EP-A-0 488840 and its corresponding U.S. Pat. No. 5,226,415, all commonly assigned to ELA Medical, the assignee of this invention. These documents describe a mode of processing atrial extra systoles ("AES") and functioning in fallback, corresponding to what is implemented in the commercial pacemaker product that is sold under the mark CHORUS II 6234 by ELA Medical, Montrouge France.

The myocardium can be subjected to what is referred to as a trouble of the atrial rhythm ("ToAR"), a generic term that covers various atrial arrhythmias including, but not limited to, tachycardia, fibrillation, and flutter. TOAR is characterised, at its detection, by a rapid atrial rhythm.

In the absence of ToAR, the pacemaker normally operates in a DDD pacing mode, that is to say with the atrium and ventricle associated (i.e., synchronized).

When one detects a ToAR, that is to say, essentially, when the atrial rhythm exceeds an acceptable (or threshold) level, the pacemaker switches to a mode called "de-synchronisation" (or "atrial-ventricular dissociation"). In the desynchronisation mode, the pacemaker stimulates the ventricle independently of the detected atrial rhythm, because the excessive atrial rhythm is considered to be pathological.

When the atrial rhythm returns to the acceptable level, the pacemaker operates a "re-synchronisation" (also called an "atrial-ventricular re-association") to return, in a progressive manner, to function in the DDD mode. It is necessary that the re-synchronisation be progressive to detect possibly an association in a 2:1 (Wenckebach) mode, in which case it would not be necessary to proceed to the re-association.

The invention concerns more particularly the control of the re-synchronisation in the fallback mode.

In known devices, such that those described in aforementioned patent documents, one re-synchronises when one no longer detects a ToAR arrhythmia. But it happens frequently that an atrial fibrillation ("AF"), originating with a ToAR, degenerates over time, and, although it remains present, in fact it no longer can be detected by the pacemaker. In this case, the pacemaker, after being correctly changed to a fallback mode (de-synchronisation) at the beginning of the ToAR arrhythmia, wrongly interprets the absence of detection of the ToAR as a disappearance of the ToAR arrhythmia, and then re-synchronises to operate in a DDD mode.

In others words, particular signal characteristics of an AF, namely, a lower amplitude, a very irregular rhythm, etc., can lead to a loss of detection of the signal that is interpreted and incorrectly managed by the pacemaker as a disappearance of the corresponding ToAR.

OBJECTS AND SUMMARY OF THE INVENTION

It is, therefore, an object of the present invention to remedy to the aforementioned difficulty, by controlling the resynchronisation, in a conditional manner, only in the presence of an effectively detected atrial rhythm, that is to say to re-synchronize only if one really detects an atrial rhythm (a true positive detection), and not solely in the absence of detection of the ToAR (with the corresponding risk of detecting a false negative).

Broadly, the invention concerns an active implantable medical device, more particularly a cardiac pacemaker, defibrillator and/or cardiovertor, having a dual chamber pacing and stimulation function, which includes:

means for determining and analyzing atrial and ventricular rhythm;

means for stimulating the atrium and the ventricle;

means for de-synchronizing the ventricular stimulation from the actual rhythm when the atrial rhythm exceeds an acceptable level; and means for progressively re-synchronizing the ventricular stimulation to the atrial rhythm in response to a return of the atrial rhythm to the acceptable level.

The means for re-synchronisation is controlled in a conditional manner, to be triggered (i.e., initiated to operate) and maintained (i.e, continuing to operate) to function only if the following condition is satisfied:

(a) the means for analysis does not detect a trouble of the atrial rhythm (ToAR).

According to a preferred embodiment of the invention, the means for re-synchronizing is triggered and maintained to function only if, in addition to condition (a), the following condition also is satisfied:

(b) the analyzing means detects the presence of an effective atrial rhythm (also referred to as an effective sinus rhythm).

Preferably, the analyzing means functions to consider whether there is a presence of an effective atrial rhythm if an atrial depolarisation is detected during at least a predetermined fraction of a given number of successive cycles. The fraction is preferably a majority fraction, and can be a programmable value.

In an alternate embodiment, the means for re-synchronizing is triggered and maintained to function only if, in addition to conditions (a) and (b), the following condition also is satisfied:

(c) the analyzing means determines that, during successive cycles in the course of the re-synchronisation phase, the duration between the end of the post-atrial atrial refractory period and the end of the atrial escape interval is at least equal to a predetermined duration, which is typically selected from between 450 and 500 ms.

BRIEF DESCRIPTION OF THE DRAWINGS

Further advantages, features and characteristics of the present invention will become apparent to a person of ordinary skill in the art from the following detailed description, made with reference to annexed drawings, in which:

FIG. 1 is a diagram showing the different intervals and the windows defined in the course of a cardiac cycle; and FIG. 2 is a flow chart of implementation of the function of fallback according to a preferred embodiment of the invention.

DETAILED DESCRIPTION OF THE DRAWINGS

The function of fallback, and particularly its implementation according to the present invention, is described with reference to FIGS. 1 and 2. Initially, the pacemaker functions in a DDD mode, that is to say with an association of the atrium and the ventricle (stage 10).

The fallback is based on the capacity of the device to differentiate a normal sinus activity (a sinus rhythm ("SR") from an atrial extra-systole (AES), that will trigger a change to the fallback mode. This type of detection (stage 12) is well known in the art and will not be described here in detail. One can refer particularly to FR-A-2,544,989, EP-A-0 488 840 and U.S. Pat. No. 5,226,415 for such details.

Essentially, one defines a window of Detection of the Acceleration of the Atrial Rhythm (DAAR) shown on FIG. 1, which is also called a "Post-Atrial Atrial Refractory Period" (PAARP).

The DAAR is a period that starts on an atrial event and has a length that is a given fraction of an average of a number of the preceding detected sinus intervals. The durations AVD and AEI correspond, respectively, to the atrio-ventricular delay (AVD) and to the atrial escape interval (AEI). A normal sinus interval or activity is defined as when an atrial event is present outside the DAAR window (as in the illustrated case in FIG. 1). Conversely, one considers that there is a possibility of trouble of the atrial rhythm (suspicion of ToAR), and therefore AES, if one detects an atrial event inside the DAAR window (not shown).

If this suspicion of ToAR is confirmed during a succession of cardiac cycles, the pacemaker changes to a "pseudo-DDI" mode (mode DDI or VVI, according to the detected ventricular rhythm). In this case, one de-synchronizes the stimulation of the ventricle from the detected atrial rhythm. The corresponding de-synchronisation (stage 14) operates to lengthen gradually the duration of the ventricular escape interval until the stimulation frequency reaches a predetermined lower frequency, for example, the base frequency or a frequency prescribed by a sensor of enslavement (a rate responsive sensor).

One proceeds then to a succession of tests (stages 16, 18 and 20) to determine whether to maintain the desynchronization mode functioning, or, on the contrary, to proceed to a mode of progressive re-synchronisation between the atrium and the ventricle.

First of all (stage 16), one insures that the atrial sensing range is effective, that is to say that one has a Window of Sensing of the Sinus Rhythm (FERS on the FIG. 1) of sufficient duration.

The FERS window is defined as the interval between the end of the DAAR/PAARP period and the appearance of a new detected atrial depolarisation. One considers that there is a range of sufficient atrial sensing if, for example, the duration of the FERS period is at least 470 ms (this value not being of course restrictive; typically, it can take a value in the range between 450 and 500 ms).

The condition that one next verifies (stage 18) is the classic absence of a ToAR condition, that would be revealed by a rapid atrial rhythm.

One knows indeed that a ToAR, which can cover various atrial arrhythmia, are all characterised, at the detection, by a rapid atrial rhythm. One insures as well that no short PP interval is detected during some number of consecutive cycles, e.g., twelve cycles. The threshold of detection of short PP intervals is typically fixed at 500 ms, a value below which one considers that the rhythm is "slow", and above which the rhythm is "rapid" and, therefore, pathological.

If one finds at least one short PP interval during the twelve consecutive intervals, then one considers that the condition of re-synchronisation is not verified, and one remains in the de-synchronised mode (a return to stage 14).

If, on the other hand, one is in the presence a slow atrial rhythm, the corresponding condition for the passage to the re-synchronisation is then verified.

The third condition (stage 20), which typically follows satisfying the two preceding conditions, is to detect that one is in the presence of a positively detected sinus rhythm ("SR"). The corresponding criterion is, for example, that one has less than x% of the detected atrial stimuli during a predetermined number of consecutive cycles; "x" can be a programmable threshold and/or take a value, for example, of 50%, that is to say that one has to have less than six atrial stimulations over the last twelve cycles examined (or, in others words, at least 50% of atrial events are detected with a long PP interval).

If the three conditions of stages 16 (an effective atrial sensing range), 18 (a slow atrial rhythm) and 20 (a detection of a sinus rhythm) are cumulatively verified, one considers that the atrial arrhythmia (ToAR) has ended. Consequently, one changes to the progressive re-synchronisation mode (stage 22), so as to accelerate little-by-little the ventricular rhythm until it reaches the atrial rhythm to find the synchronism. Management of the AEI for that purpose is described, for example, in the aforementioned patent documents, to which one will be able to refer, and it is in itself well known.

This phase of re-synchronisation (stage 22) is not, however, maintained until it has resynchronized, unless, on the one hand, the atrial sensing range is always effective (stage 24, similar to the stage 16 in its implementation), and, on the other hand, there has been no short PP interval during the twelve consecutive cycles (stage 26, similar to the stage 18 for its implementation).

If these two conditions are cumulatively verified, the ventricular simulation is re-associated to the atrial rhythm in the DDD mode (a return to the stage 10).

On the other hand, if the sensing is ineffective, or if one detects again one or more short PP intervals, one then returns to the fallback mode (operating in a DDI or VVI mode) (stage 14), until the three conditions of re-association (stages 16, 18 and 20) indicated above are again verified.

One skilled in the art will appreciate the present invention can be practiced by other than the described embodiments, which are presented for purposes of illustration and not of limitation, and the numbers and values used in the described embodiments are exemplary and not limiting, and may be varied without departing from the present invention.

We claim:

1. An active implantable medical device including an atrial stimulation function and a ventricular stimulation function, comprising:

analyzing means for detecting atrial and ventricular events, analyzing detected atrial and ventricular events and determining an atrial rhythm and a ventricular rhythm;

wherein the analyzing means comprises means for determining if a determined atrial rhythm is an effective sinus rhythm and means for determining if a detected atrial rhythm is a trouble of atrial rhythm;

means (14) for de-synchronizing the ventricular stimulation from the atrial rhythm when the atrial rhythm exceeds a predetermined level;

means (22) for progressively re-synchronizing the ventricular stimulation to the atrial rhythm in response to a return of the atrial rhythm to the predetermined level; and means for controlling the re-synchronizing means to trigger and maintain resynchronization if:
  a) the analyzing means detects (18, 26) no trouble of the atrial rhythm, and
  b) the analyzing means detects (20) an effective sinus rhythm.

2. The device of claim 1, wherein the analyzing means detects atrial depolarisations and the controlling means further comprises means for considering that there is an effective sinus rhythm if at least one atrial depolarisation is detected during at least a predetermined fraction of a given number of successive cycles.

3. The device of claim 2, wherein the predetermined fraction is a majority fraction.

4. The device of claim 2, wherein the predetermined fraction is a programmable fraction.

5. The device of claim 1, wherein the controlling means triggers and maintains said re-synchronizing means to function if, in addition to conditions (a) and (b):
  c) the analyzing means determines (16, 24) a duration (FERS), between an end of a post-atrial atrial refractory period and an end of an atrial escape interval, and determines that said duration (FERS) is at least equal to a predetermined duration during a successive number of cycles in the course of progressively resynchronizing the ventricular stimulation to the atrial rhythm.

6. The device of claim 5, wherein the predetermined duration is selected from between 450 and 500 ms.

7. A method of controlling the fallback mode of an active implantable medical device having a dual chamber stimulation function including ventricular stimulation, comprising:

monitoring and analyzing atrial and ventricular events;

determining an atrial rhythm and a ventricular rhythm from said analyzed atrial and ventricular events;

comparing the atrial rhythm to a predetermined level;

de-synchronizing the ventricular stimulation from the atrial rhythm when the atrial rhythm exceeds the predetermined level;

progressively re-synchronizing the ventricular stimulation to the atrial rhythm in response to a return of the atrial rhythm returning to the predetermined level;

determining if the atrial rhythm includes no trouble of the atrial rhythm;

determining if the atrial rhythm includes an effective sinus of the atrial rhythm; and controlling the re-synchronization to trigger and maintain resynchronization in response to:
  a) detecting (18, 26) no trouble of the atrial rhythm, and
  b) detecting (20) an effective sinus rhythm.

8. The method of claim 7, wherein detecting an effective sinus rhythm further comprises detecting at least one atrial depolarisation during at least a predetermined fraction of a given number of successive cycles.

9. The method of claim 8, further comprising providing said determined fraction to be a majority fraction.

10. The method of claim 8, wherein providing said predetermined fraction further comprises programming a fraction.

11. The method of claim 7, further comprising conditioning the triggering and maintaining of the condition re-synchronation on:
  c) determining a duration (FERS) between an end of a post-atrial atrial refractory period and an end of an atrial escape interval, and determining that said duration (FERS) is at least equal to a predetermined duration during a successive number of cycles during progressively resynchronizing the ventricular stimulation to the atrial rhythm.

12. The method of claim 11 further comprising selecting the predetermined duration from between 450 and 500 ms.

13. An implantable cardiac pacemaker having an atrial sensing function, an atrial stimulation function, a ventricular sensing function and a ventricular stimulation function and a fallback mode including a resynchronization of a ventricular stimulation to an atrial rhythm, controlled in accordance with the method of any of claims 7, 8, 9, 10 11 and 12.

* * * * *

UNITED STATES PATENT AND TRADEMARK OFFICE
CERTIFICATE OF CORRECTION

PATENT NO. : 5,931,856
DATED : August 3, 1999
INVENTOR(S) : Anne Bouhour and Marcel Limousin It is certified that error appears in the above-identified patent and that said Letters Patent is hereby corrected as shown below:

Column 1,
Line 32, delete "TOAR" and insert -- ToAR -- therefor;
Line 54, delete "such that" and insert -- such as -- therefor;

Column 2,
Line 7, delete "remedy to" and insert -- remedy the -- therefor;

Column 4,
Line 10, delete "presence a" and insert -- presence of a -- therefor;
Line 43, delete "simulation" and insert -- stimulation -- therefor;

Column 6,
Line 29, delete "atrial refractory" and insert -- refractory -- therefor; and
Line 27, delete "re-synchronation" and insert -- re-synchronization -- therefor.

Signed and Sealed this

Twenty-seventh Day of July, 2004

JON W. DUDAS
*Acting Director of the United States Patent and Trademark Office*